United States Patent [19]
McVay

[11] Patent Number: 5,437,654
[45] Date of Patent: Aug. 1, 1995

[54] IRRIGATION SET

[75] Inventor: William P. McVay, Ashland, Pa.

[73] Assignee: Advanced Surgical Products, Inc., Miami, Fla.

[21] Appl. No.: 118,653

[22] Filed: Sep. 10, 1993

[51] Int. Cl.[6] .............................................. A61M 39/00
[52] U.S. Cl. ................................ 604/403; 604/131; 604/406; 604/247; 222/189.06
[58] Field of Search ................... 604/19, 27, 48, 73, 604/131, 140, 147, 151, 247, 403–416; 215/228, 260, 262, DIG. 3; 220/203, 204, 209, 254, 303; 222/189

[56] References Cited

U.S. PATENT DOCUMENTS

| | | | |
|---|---|---|---|
| 2,589,728 | 3/1952 | Pratt | 604/131 |
| 2,848,996 | 11/1956 | Kowal | 604/403 |
| 3,047,178 | 7/1962 | Poitras et al. | 215/262 |
| 3,227,173 | 1/1966 | Bernstein | 215/DIG. 3 |
| 3,467,270 | 9/1969 | Eady | 604/403 |
| 4,838,875 | 6/1989 | Somor | 604/408 |
| 4,997,429 | 3/1991 | Dickerhoff et al. | 604/405 |
| 5,041,105 | 8/1991 | D'Alo et al. | 604/411 |
| 5,041,106 | 8/1991 | Noji et al. | 604/411 |

Primary Examiner—C. Fred Rosenbaum
Assistant Examiner—Perry E. Van Over
Attorney, Agent, or Firm—Keck, Mahin & Cate

[57] ABSTRACT

An irrigation set for use with a laparoscopic and/or hysteroscopic irrigation pump includes a bottle cap having an open mouth, closed-end cup shape threaded on the inside surface and defining a region just inside the closed end provided with an undercut and an opening defined in the closed end. A disk assembly is composed of a disk received in the region and retained therein by the undercut. The side of said disk inside the cap defines a depending skirt. The disk defines a first opening aligned with the depending skirt, a check valve cartridge and draw tube secured to the depending skirt. A first tubular projection on the disk is aligned with the first opening and projects through the opening in the closed end. A second tubular projection on the disk is aligned with the second opening and projects through the tubular opening in the closed end. A gas tubing is secured at one end to the second tubular projection, and a gas fitting is secured to the other end of the gas tubing. An annular gasket is secured to the side of the disk, about the peripheral portion thereof, to seal the mouth of a bottle. The first tubular projection is connected by tubing with an irrigation probe. Finally, a cap assembly is provided for an irrigation.

7 Claims, 2 Drawing Sheets

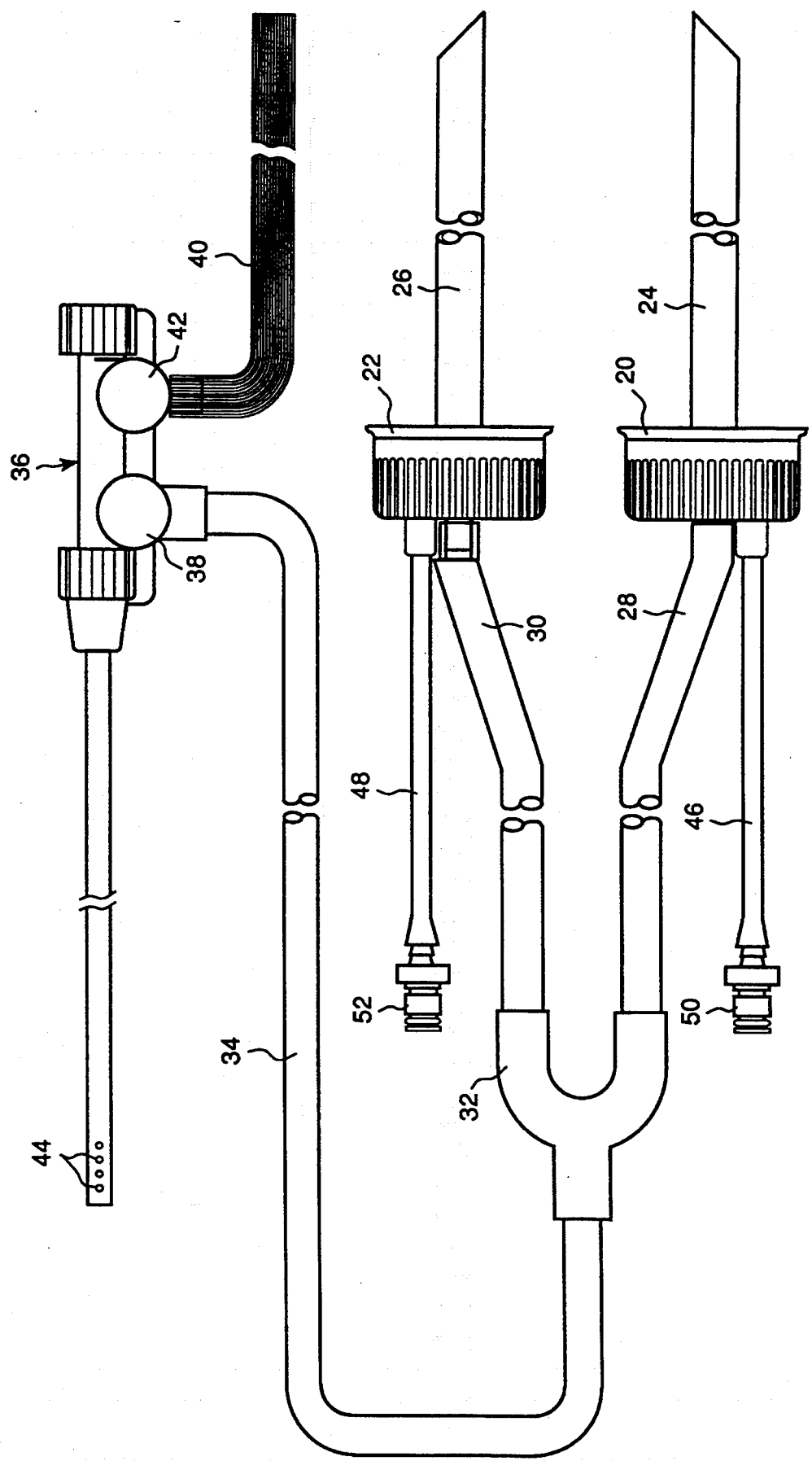

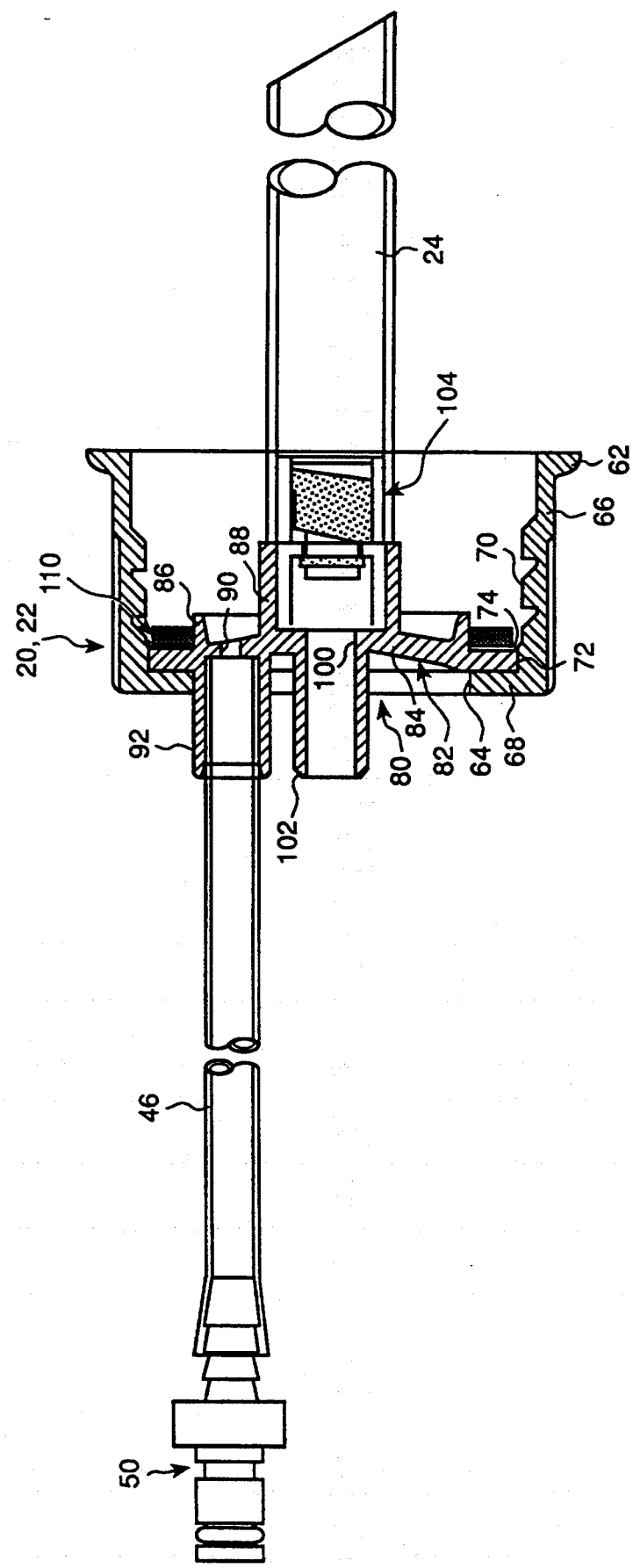

IRRIGATION SET

FIELD OF INVENTION

The present invention relates to a novel irrigation set for use with an endoscopic (including laparoscopic and/or hysteroscopic) irrigation pump.

BACKGROUND OF INVENTION

A laparoscopic irrigation pump requires the use of a single patient irrigation set with attached laparoscopic probe in order to irrigate or lavage the interior of the abdomen during laparoscopic surgery. The prob incorporates two trumpet valves, one of which turns on and off the flow of solution coming from the plastic irrigation bottles which contain sterile, physiological solution. The other trumpet valve controls the vacuum or suction so that the probe removes excessive solution from the abdomen as well as smoke, blood clots and tissue debris. This material is collected in a vacuum canister many of which are currently on the market for surgical applications. The irrigation probe itself has been used since 1986 in one form or another for laparoscopic surgery. In use, problems have been experienced with the irrigation sets.

SUMMARY OF THE INVENTION

The novel irrigation set of the present invention is designed so that two solution bottles can be attached to each tubing going to the "Y" connector via a novel cap assembly. The cap assembly is unique for the following reason. During assembly to the physiological solution bottles the cap does not twist or turn the tubing lines emerging from the top of the cap assembly since it consists of two parts: (1) a disk assembly which incorporates a sealing gasket, a check valve cartridge, a gas tubing assembly and a flexible draw tube and (2) a bottle cap with threads which mate to the appropriate bottle. The current caps on the market require the user to twist the bottle in order to assemble it to the cap and prevent tubing line twists. This is due to the fact that they are machined from one piece of stainless steel.

Since the diameter of the disk is smaller than the inner diameter of the bottle cap, the cap can be twisted independently of the disk assembly, thus assuring that the disk and attached tubing lines will not twist during attachment to a solution bottle. The user finds that this feature allows them to twist the cap in a normal manner and also to position the emerging lines to a desired angle relative to the bottle.

The disk assembly and cap are assembled during production by simply snapping the disk past small undercuts molded within the cap. This allows rotational movement yet prevent the cap from sliding up the tubing lines and potentially being contaminated if the lines should touch a non-sterile surface. The user can pick up the entire cap and disk assembly by the cap rather than by the tubing if this feature was not created. Since the user could exchange empty bottles for full ones quite frequently during an operation, a user friendly bottle cap would be appreciated.

Secondly, the cap assembly is made from low-cost plastic components or plastic resins which allows the disposal of the unit after each patient. Currently marketed caps are made from stainless steel and require cleaning and steam autoclaving prior to each use. The rubber gaskets in the caps eventually tear and pieces of debris can fall into the sterile solution and potentially contaminate the abdomen if they should be washed up the draw tube. Leakage between the cap and bottle can also result from poor maintenance of this gasket. The single patient use feature of the disclosed design improves the reliability and safety of the system.

The third feature of the cap assembly allows the user to fit the bottle to a range of solution bottle sizes or lengths. For instance Baxter-Travenol Laboratories makes solution bottles in 1.0 and 1.5 liter sizes, which have different total heights. Also, Abbott Laboratories supplies solution in 1.0 liter bottles which are different in height than Baxter-Travenol's bottles. Currently marketed units incorporate rigid stainless steel draw tubes which are sized for the appropriate bottle manufacturer and size. Thus the user must change the cap variety if it switches to a different bottle make.

This cap assembly incorporates a flexible plastic draw tube which is long enough for the longest bottle yet due to its flexibility can be used in shorter bottles without penalty.

Other and further advantages of the invention will be apparent from the following detailed description taken in conjunction with the drawings.

DESCRIPTION OF DRAWINGS

FIG. 1 is a schematic of the novel irrigation set.

FIG. 2 is a section through a cap assembly of the irrigation set depicted in FIG. 1.

DETAILED DESCRIPTION OF PREFERRED EMBODIMENT

Referring now to the drawings, the novel irrigation set consists of a pair of bottle caps 20 and 22 provide with flexible draw tubes 24 and 26. Liquid tubes 28 and 30 are attached at one end to caps 20 and 22 and at their other ends are connected to a wye 32 which in turn is connected via a tubing 34 to a suction probe 36 through a trumpet valve 38. A suction tube 40 connects to a second trumpet valve 42. The probe is provided with holes 44 adjacent its free end. Gas tubing 46 and 48 is also connected to caps 20 and 22 and each is provided with a suitable fitting 50 and 52 and its free end.

The details of the cap assembly are shown in FIG. 2. Each cap 20, 22 consists of a cup-shaped plastic molding 60 consisting in turn of a skirt portion 66 and a closed-end portion 68, terminating in a slightly flared out rim 62 and provided with an opening 64 through its closed end 68. The inside surface of skirt portion 66 is provided with threads 70 to enable the cap 20 to be screwed onto a bottle. The area 72 next to the inside surface of closed end 68 is of smaller diameter than the threads 70 and is provided with an undercut 74 that is molded with the cap and provides a slightly reduced diameter or restriction at the side of area 72 remote from closed end 68. A disk assembly 80, consisting of a disk 82 having a concave central portion 84 and defining a depending short outer skirt 86 and long inner skirt 88, is received in area 72 and lies next to closed end 68 with skirts 86 and 88 disposed on the side of disk 82 away from the closed end 68. The diameter of disk 82 is slightly greater than the diameter of the opening or restriction afforded by undercut 74 and the thickness or depth of area 72 is just great enough to accommodate disk 82.

A hole 90 is defined in the concave region 84 of disk 82 in the annular space between skirts 86 and 88. Coaxially aligned with hole 90 is an integral tubular projection 92 to which gas tubing 46 terminating with fitting 50 is fixed such as by cementing. A central hole 100 is defined in concave region 84 axially of the cap and lies coaxial with skirt 88 but of smaller diameter. A tubular projection 102 is coaxially aligned with hole 100, and serves as a connection for liquid tubing 28. A check valve cartridge 104 is located and fixed in skirt 88 such as by cementing and draw tube 24 is fixed to cartridge 104 and skirt 88 such as by cementing. An annular gasket 110 is secured to the outer peripheral portion of the inside surface of disk 80 surrounding skirt 86, to seal against the lip or rim defining the mouth or opening of a bottle containing irrigation solution.

The cap is assembled by inserting the disk assembly into the open mouth of the cap and pressing inwardly until the disk periphery snaps past the undercut rim (or series of peripherally spaced undercuts). By means of this novel structure, the cap can rotate relative to the disk assembly. The advantages are previously detailed.

Although the invention has been described in terms of a preferred embodiment, nevertheless, changes and modifications are possible which do not depart from the spirit or scope of the inventive concepts taught herein. Such changes and modifications are deemed to fall within the purview of the claims.

What is claimed is:

1. An irrigation set for use with and endoscopic irrigation pump, comprising:
 a bottle cap having an open mouth, closed-end cup shape being threaded on the inside surface and defining a region just inside the closed end provided with an undercut and an opening defined in the closed end,
 a disk assembly composed of a disk that is received in said region and retained therein by the undercut while allowing relative rotation between the bottle Cap and the disk and preventing relative translation between the bottle cap and the disk, the side of said disk inside the cap defining a depending skin, said disk defining a first opening aligned with the depending skirt, a check valve cartridge and draw tube secured to said depending skirt, a first tubular projection on the disk aligned with the first opening and projecting through the opening the in the closed end, a second tubular projection on the disk aligned with a second opening and projecting through the opening in the closed end, a gas tubing secured at one end to the second tubular projections a gas fitting secured to the other end of the gas tubing, an annular gasket secured to the side of the disk inside the cap about the peripheral portion thereof to seal the mouth of a bottle, and
 tubing means for connecting the first tubular projection with an irrigation probe.

2. An irrigation set for use with an endoscopic irrigation pump, comprising:
 a bottle cap having an open mouth, closed-end cup shape being threaded on the inside surface and defining a region just inside the closed end provided with an undercut and an opening defined in the closed end,
 a disk assembly composed of a disk that is received in said region and retained therein by the undercut while allowing relative rotation between the bottle cap and the disk and preventing relative translation between the bottle cap and the disk, said disk defining a first opening and a second opening, a check valve cartridge and serially mounted draw tube secured to one side of the disk aligned with said first opening, a first tubular projection on the other side of the disk aligned with the first opening and projecting through the opening in the closed end, a second tubular projection on the other side Of the disk aligned with the second opening and projecting through the opening in the closed end, a gas tubing secured at one end to the second tubular projection, and a gas fitting secured to the other end of the gas tubing,
 an annular gasket secured to said one side of the disk about its peripheral portion thereof to seal the mouth of a bottle, and
 tubing means for connecting the first tubular projection with an irrigation probe.

3. A cap assembly for use as a component of an irrigation set used with an endoscopic irrigation pump, comprising:
 a bottle cap having an open mouth, closed-end cup shape being threaded on the inside surface and defining a region just inside the closed end provided with an undercut and an opening defined in the closed end,
 a disk assembly composed of a disk that is received in said region and retained therein by the undercut while allowing relative rotation between the bottle cap and the disk and preventing relative translation between the bottle cap and the disk, said disk defining a first opening and a second opening, a check valve cartridge and serially mounted draw tube secured to one side of said disk aligned with said first opening, a first tubular projection on the other side of the disk aligned with the first opening and projecting through the opening in the closed end, a second tubular projection on the other side of the disk aligned with the second opening and projecting through the opening in the closed end, a gas tubing secured at one end to the second tubular projection, and a gas fitting secured to the other end of the gas tubing, and
 an annular gasket secured to said one side of the disk about its peripheral portion thereof to seal the mouth of a bottle.

4. A cap assembly for use as a component of an irrigation set for use with an endoscopic irrigation pump, comprising:
 a bottle cap having an open mouth, closed-end cup shape being threaded on the inside surface and defining a region just inside the closed end provided with an undercut and an opening defined in the closed end,
 a disk assembly composed of a disk that is received in said region and retained therein by the undercut while allowing relative rotation between the bottle caps and the disk and preventing relative translation between the bottle cap and the disks, the side of said disk inside the cap defining a depending skirt, said disk defining a first opening aligned with the depending skirt and a second opening laterally outside the depending skirt, a check valve cartridge and serially mounted draw tube secured to said depending skin, a first tubular projection on the disk aligned with the first opening and projecting through the opening in the closed end, a second tubular projection on the disk aligned with the second opening and projecting through the tubular opening in the closed end, a gas tubing secured at one end to the second tubular projection, and a gas fitting secured to the other end of the gas tubing, and an annular gasket secured to the side of the disk inside the cap about the peripheral portion thereof to seal the mouth of a bottle.

5. A cap assembly for use as a component of an irrigation set used with an endoscopic irrigation pump, comprising:

a bottle cap having an open mouth, closed-end cup shape being threaded on the inside surface and an opening defined in the closed end, a disk assembly composed of a disk receive in said bottle caps, said disk defining a first opening and a second opening, a check valve cartridge and serially mounted draw tube secured to one side of said disk aligned with said first opening, a first tubular projection on the other side of the disk aligned with the first opening and projecting through the opening in the closed end, a second tubular projection on the other side of the disk aligned with the second opening and projecting through the opening in the closed end, a gas tubing secured at one end to the second tubular projection, and a gas fitting secured to the other end of the gas tubing, an annular gasket secured to said one side of the disk about its peripheral portion thereof to seal the mouth of a bottle, and said bottle cap and disk defining mutually cooperating portions including an undercut which results in the disk being in a captured relationship with respect to the bottle cap while enabling relative rotation between the bottle cap and disk and preventing relative translation between the bottle cap and the disk.

6. A cap assembly for use as a component of an irrigation set for use with a endoscopic irrigation pump, comprising:

a bottle cap having an open mouth, closed-end cup shape being threaded on the inside surface and an opening defined in the closed end, a disk assembly composed of a disk that is received in said bottle cap, the side of said disk inside the cap defining a depending skirt, said disk defining a first opening aligned with the depending skirt and a second opening laterally outside the depending skirt, a check valve cartridge and serially mounted draw tube secured to said depending skirt, a first tubular projection on the disk aligned with the first opening and projecting through the opening in the closed end, a second tubular projection on the disk aligned with the second opening and projecting through the tubular opening in the closed end, a gas tubing secured at one end to the second tubular projection, and a gas fitting secured to the other end of the gas tubing, an annular gasket secured to the side of the disk inside the cap about the peripheral portion thereof to seal the mouth of a bottle, and said bottle cap and disk defining mutually cooperating portions which result in the disk being captured by the bottle cap while enabling relative rotation there between without relative translation there between.

7. An irrigation set for use with and endoscopic irrigation pump, comprising:

a bottle cap having an open mouth, closed-end cup shape being threaded on the inside surface and an opening defined in the closed end, a disk assembly composed of a disk that is received in said bottle cap and retained therein by mutually cooperating portions defined in the bottle cap and disk which allow relative rotation between the bottle cap and the disk and prevents relative translation between the bottle cap and the disk, the side of said disk inside the cap defining a depending skirt, said disk defining a first opening aligned with the depending skirt and a second opening laterally displaced from the first opening, a check valve cartridge and draw tube secured to said depending skirt, a first tubular projection on the disk aligned with the first opening and projecting through the opening the in the closed end, a second tubular projection on the disk aligned with the second opening and projecting through the tubular opening in the closed end, a gas tubing secured at one end to the second tubular projections a gas fitting secured to the other end of the gas tubing, an annular gasket secured to the disk about its peripheral portion to seal the mouth of a bottle, and tubing means for connecting the first tubular projection with an irrigation probe.

* * * * *